(12) United States Patent
Teoh et al.

(10) Patent No.: US 10,956,539 B2
(45) Date of Patent: Mar. 23, 2021

(54) NUTRITION TRACKING SYSTEM

(71) Applicant: Under Armour, Inc., Baltimore, MD (US)

(72) Inventors: Alison Teoh, San Francisco, CA (US); Jason Buckner, San Francisco, CA (US); Nick Crocker, San Francisco, CA (US); Paul Radcliffe, San Francisco, CA (US)

(73) Assignee: Under Armour, Inc., Baltimore, MD (US)

( * ) Notice: Subject to any disclaimer, the term of this patent is extended or adjusted under 35 U.S.C. 154(b) by 358 days.

(21) Appl. No.: 15/695,677

(22) Filed: Sep. 5, 2017

(65) Prior Publication Data
US 2018/0082040 A1    Mar. 22, 2018

Related U.S. Application Data

(60) Provisional application No. 62/396,527, filed on Sep. 19, 2016.

(51) Int. Cl.
| *G06F 19/00* | (2018.01) |
| *G09B 19/00* | (2006.01) |
| *G16H 20/60* | (2018.01) |
| *G16H 40/63* | (2018.01) |
| *G16H 40/67* | (2018.01) |
| *G06Q 10/10* | (2012.01) |

(52) U.S. Cl.
CPC ..... *G06F 19/3475* (2013.01); *G06Q 10/1093* (2013.01); *G09B 19/0092* (2013.01); *G16H 20/60* (2018.01); *G16H 40/63* (2018.01); *G16H 40/67* (2018.01)

(58) Field of Classification Search
CPC ............ G09B 19/0092; G06F 19/3475; G16H 20/60; G16H 50/30
See application file for complete search history.

(56) References Cited

U.S. PATENT DOCUMENTS

| 2011/0202359 | A1* | 8/2011 | Rak | G16H 20/60 705/1.1 |
| 2012/0254196 | A1* | 10/2012 | Abramski | G06F 19/3475 707/748 |
| 2014/0322678 | A1* | 10/2014 | Briancon | G09B 19/0092 434/127 |
| 2016/0103910 | A1 | 4/2016 | Kim et al. | |
| 2016/0379520 | A1* | 12/2016 | Borel | G09B 19/0092 434/127 |

* cited by examiner

*Primary Examiner* — Jerry-Daryl Fletcher
(74) *Attorney, Agent, or Firm* — Maginot, Moore & Beck LLP (57) ABSTRACT

Methods and apparatus for nutrition tracking. In one exemplary embodiment, a methods and apparatus for nutrition tracking are provided which receive selections of consumable items from a user, identify at least one item to be purposefully omitted in nutrition calculation, and calculate total nutrition for a period of time based on the selections. The calculation comprises purposeful omission of the nutritional data of the identified at least one of the plurality of consumable items. In order to accomplish the calculation, each of the selected items is associated with a data record in a database, each data record in the database comprising nutritional data regarding a consumable item to which the data record corresponds.

19 Claims, 7 Drawing Sheets

NUTRITION TRACKING SYSTEM

CROSS-REFERENCE TO RELATED APPLICATION

This application claims priority from U.S. provisional patent application No. 62/396,527, filed Sep. 19, 2016, the entire disclosure of which is hereby incorporated by reference in its entirety.

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

The method, apparatus, and system disclosed in health tracking systems and, more particularly, to a method for enabling a user to log items in a health tracking system without having those items used in a nutrition and/or calorie count for the day.

BACKGROUND

In recent years, health and fitness tracking applications that track food consumption have become very popular. Food consumption is important to a healthy lifestyle and is known to be related to various health conditions, such as diabetes and obesity to name a few. Health and fitness tracking applications allow users to set and achieve personalized health goals by tracking the foods and beverages that they consume. These applications enable users to gain insights that help them make smarter choices and create healthier habits.

One challenge that exists for such health and fitness tracking applications is encouraging users to consistently and honestly track the foods and beverages that they consume. On occasion, users have days or meals during which they consume foods and beverages that they know to be unhealthy, are consumed in excess, or are otherwise adverse to their health goals (such occasions are sometimes referred to as "cheat days" or "cheat meals"). If the user choses to track those unhealthy foods and beverages, the health and fitness tracking applications may indicate that the user has failed to meet one or more of their health goals. In order to avoid feelings of guilt and failure, it is very tempting for the user to simply neglect to track these unhealthy foods and beverages. As a result, the users' food diaries are sometimes incomplete and do not provide an accurate picture of the users' consumption habits. In addition, if the user decides not to track a food or beverage, it may lead to more frequent decisions to not track foods and beverages in the future and eventually to complete abandonment of tracking of foods and beverages.

In view of the foregoing, it would be advantageous to provide a method of tracking foods and beverages that encourages users to track all foods and beverages consumed by the user, including foods and beverages that are unhealthy, consumed in excess or otherwise adverse to the user's own health goals.

SUMMARY

In a first aspect of the disclosure, a method of operating a health tracking system is disclosed. In one embodiment, the method comprises: (i) receiving a plurality of consumable item selections associated with a period of time, each of the plurality of consumable item selections associated with a data record in a database, each data record in the database comprising nutritional data regarding a consumable item to which the data record corresponds; (ii) identifying at least one of the plurality of consumable item selections to be purposefully omitted from calculations relating to the period of time; and (iii) calculating a first metric based on the nutritional data regarding the plurality of consumable item selections, the calculation comprising purposeful omission of the nutritional data of the identified at least one of the plurality of consumable items.

In a second aspect of the disclosure, a health tracking system is disclosed. In one embodiment, the system comprises: a database configured to store a plurality of data records, each data record in the database comprising nutritional data regarding a consumable item to which the data record corresponds; and a data processor in communication with the database, the data processor configured to: (i) receive a plurality of consumable item selections, each of the plurality of consumable item selections being associated with a period of time, and each of the plurality of consumable item selections being associated with a data record in the database, (ii) identify at least one of the plurality of consumable item selections as a selection which will be purposefully omitted during the calculation of a first metric, and (iii) calculate the first metric based on the nutritional data in the data records associated to those ones of the plurality of consumable item selections which are not identified as being purposefully omitted.

In another aspect of the disclosure, a non-transitory computer-readable medium for operating a health tracking system is provided. In one embodiment, the computer-readable medium comprises a plurality of instructions stored thereon that, when executed by a processor, cause the processor to: (i) receive, from a user, a plurality of consumable item selections associated with a period of time; (ii) associate each of the plurality of consumable item selections to a data record in a database, each data record in the database comprising a plurality of nutritional data; (iii) enable the user to identify one or more of the plurality of consumable item selections; (iv) cause the nutritional data associated to the identified one or more of the plurality of consumable item selections to be temporarily set to zero; (v) add the nutritional data of each of the plurality of consumable items to arrive at a total nutritional data for the period of time; and (vi) cause the total nutritional data to be displayed to the user.

These and other aspects will be apparent given the following disclosure.

BRIEF DESCRIPTION OF THE DRAWINGS

The foregoing aspects and other features of a health and fitness tracking system are explained in the following description, taken in connection with the accompanying drawings.

All Figures © Under Armour, Inc. 2016. All rights reserved.

DETAILED DESCRIPTION

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as may normally occur to one skilled in the art which this disclosure pertains.

Disclosed embodiments include systems, apparatus, and methods associated with health and fitness tracking in general and, in particular, a system for enabling health and fitness tracking for a user.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It is noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art will readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description is not to be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C).

The terms "comprising," "including," "having," and the like, as used with respect to embodiments of the present disclosure, are synonymous.

As used herein, the term "consumable" or "consumable item" refers to foods, beverages, dietary supplements, vitamin supplements, medication, and other items for consumption. As used herein, the phrase "consumable record" or "consumable item record" refers to a data record comprising information relating to a particular consumable. Each consumable record comprises a plurality of data fields that relate to a particular consumable. In some embodiments, the consumable record includes a description field that includes data, such as a text string, that identifies or describes the particular consumable. In some embodiments, each consumable record includes fields for caloric content, macronutrients, micronutrients, serving size, and other nutrition and health information.

Health Tracking System

Figure 1:
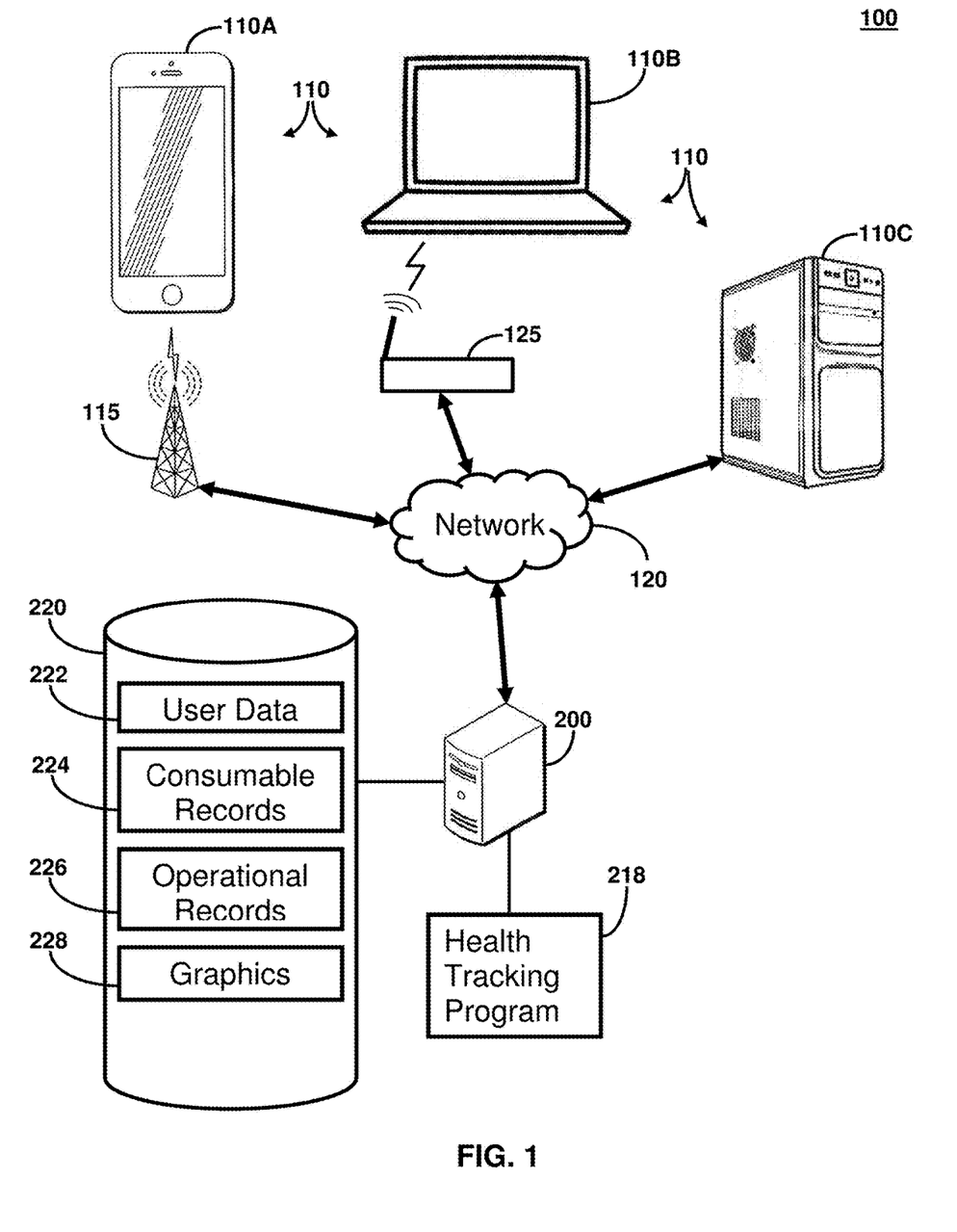
FIG. 1 is a block diagram illustrating a health tracking system in accordance with the present disclosure.

With reference to FIG. 1, an exemplary embodiment of a health tracking system 100 including functionality for enabling a user to log items in a health tracking system without having those items used in a nutrition and/or calorie count for the day. In the illustrated embodiment, the health tracking system 100 includes a plurality of health tracking devices 110 in communication with a system server 200 or other data processing system over a network 120 such as, e.g. the Internet.

The server 200 comprises a computerized device or data processing system configured to run one or more software applications on a processor thereof (e.g. the network-side health tracking program 218). The server 200 of the present embodiment is further configured to receive data relating to a selection of individual ones of a plurality of consumable records from the health tracking devices 110. In one embodiment, the consumable records are each associated to caloric and nutritional data relating to respective ones of a plurality of consumable items. The consumable records are stored at a storage apparatus or memory of the server 200 (e.g., consumable records 224).

The storage apparatus or memory of the server 200 is configured to store instructions including the network-side health tracking program 218 (which may also be referred to herein as the "health tracking application"), as well as a database 220 accessible by at least the health tracking program 218. The database 220 includes user data 222, consumable records 224, operational records 226, and graphics 228 as will be discussed in greater detail below with respect to FIG. 2. Alternatively, the server 200 may be in communication with a separate storage entity (not shown) for storage thereof.

The health tracking devices 110 (which may also be referred to herein as "health and fitness tracking devices") comprise any number of computerized apparatus which include a user interface such as, e.g., a smartphone 110A, laptop computer 110B, a tablet computer, a desktop computer 110C, or other such device. In at least one embodiment, the user interface may comprise an LCD touch screen or the like, a mouse or other pointing device, a keyboard or other keypad, speakers, and a microphone, as will be recognized by those of ordinary skill in the art. The user interface provides the user with any of various health, fitness and activity related data such as food and nutritional consumption, calorie expenditure, sleep metrics, weight, body fat, heart rate, distance travelled, steps taken, etc. In order to connect to the network 120, as demonstrated in FIG. 1, the health tracking devices 110 are generally configured to utilize any of various wired or wireless communications components, infrastructures and systems, such as cell towers 115 of a mobile telephony network, wireless routers 125, Bluetooth®, near field communication (NFC), or physical cables. Health tracking devices 110 may use data collected from sensors associated to or in communication with the health tracking device 110, such as heart rate monitors, step counters, stair counters, global positioning system ("GPS") tracking devices, as well as various other motion tracking and biometric monitoring devices; alternatively, or in addition, a user may manually enter health related data. Such sensors allow the user to easily track and automatically log activity and/or consumption information with the health tracking device.

The health tracking devices 110 are configured to communicate with the system server 200 in order to enable: accessing and searching of the consumable records 224 stored thereat, display of the consumable records, provide additional consumable records, and/or enable the user to select individual ones of the displayed consumable records for the purposes of caloric and nutritional logging. In one embodiment, foregoing functions are performed via execution of one or more software applications at the server 200 (i.e., server or network-side applications) in communication with one or more complementary software applications at the health tracking devices 110 (i.e., client-side applications). For example, the health tracking program 218, running on the processor (of the server 200) may be utilized to accomplish the foregoing, as explained in further detail below. Alternatively, or in addition, the client-side software application for performing various functions necessary for the herein disclosed concepts may also be utilized (e.g., see health tracking application 316 of FIG. 3, discussed below). Accordingly, it will be recognized that any of various processing described herein as being performed at the server 200 may alternatively be provided on a health tracking device, and vice-versa, in order to accomplish the desired functionality of the health tracking system 100, as described herein.

System Server

Figure 2:
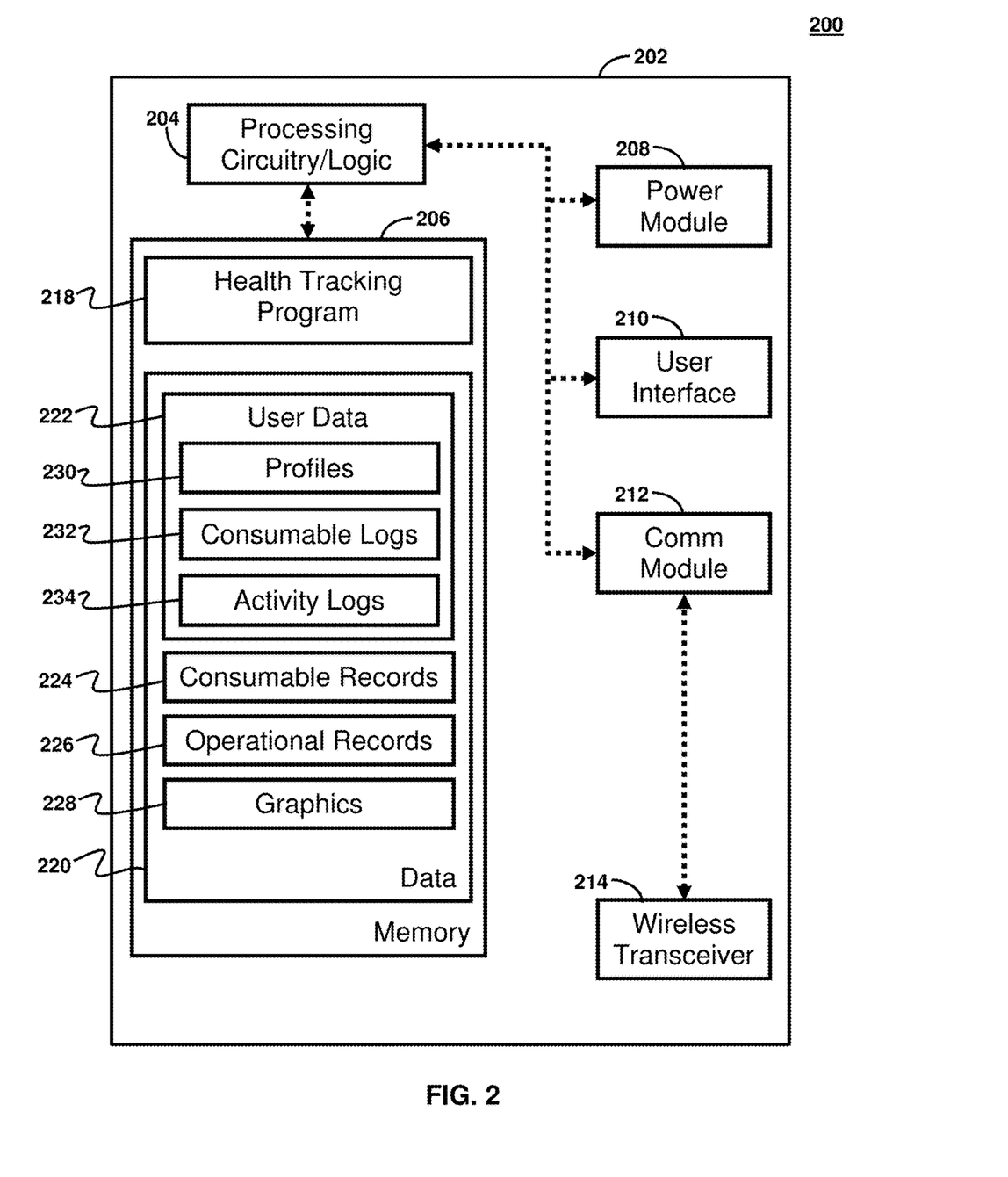
FIG. 2 is a block diagram illustrating an exemplary system server or data processing system of the health tracking system of FIG. 1.

With reference now to FIG. 2, a block diagram of an exemplary embodiment of the system server 200 of FIG. 1 is shown. It is appreciated that the embodiment of the system server 200 shown in FIG. 2 is only one exemplary embodiment of a system server 200. As such, the exemplary embodiment of the system server 200 of FIG. 2 is merely representative of any of various manners or configurations of system servers or other data processing systems that are operative in the manner set forth herein.

The system server 200 of FIG. 2 is typically provided in a housing, cabinet or the like 202 that is configured in a typical manner for a server or related computing device. In one embodiment, the system server 200 includes processing circuitry/logic 204, memory 206, a power module 208, a user interface 210, a network communications module 212, and a wireless transceiver 214.

The processing circuitry/logic 204 is operative, configured and/or adapted to operate the system server 200 including the features, functionality, characteristics and/or the like as described herein. To this end, the processing circuitry/logic 204 is operably connected to the memory 206, the power module 208, the user interface 210, the network communications module 212, and the wireless transceiver 214. The memory 206 may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. The memory 206 is configured to store instructions including a network-side health tracking application 218 for execution by the processing circuitry/logic 204, as well as a database 220 for use by at least the health tracking program 218. The database 220 includes user data 222, consumable records 224, operational records 226, and graphics 228.

With continued reference to FIG. 2, the power module 208 of the system server 200 is operative, adapted and/or configured to supply appropriate electricity to the system server 200 (i.e., including the various components of the system server 200). The power module 208 may operate on standard 120 volt AC electricity, but may alternatively operate on other AC voltages or include DC power supplied by a battery or batteries.

The network communication module 212 of the system server 200 provides an interface that allows for communication with any of various devices using various means. In particular, the network communications module 212 includes a local area network port that allows for communication with any of various local computers housed in the same or nearby facility. In some embodiments, the network communications module 212 further includes a wide area network port that allows for communications with remote computers over the Internet (e.g., network 120 of FIG. 1). Alternatively, the system server 200 communicates with the network 120 via a modem and/or router of the local area network. In one embodiment, the network communications module is equipped with a Wi-Fi transceiver 214 or other wireless communications device. Accordingly, it will be appreciated that communications with the system server 200 may occur via wired communications or via the wireless communications. Communications may be accomplished using any of various known communications protocols. In the embodiment of FIG. 2, the wireless transceiver 214 may be a Wi-Fi transceiver, but it will be recognized that the wireless transceiver may alternatively use a different communications protocol.

The system server 200 may be accessed locally by an authorized user (i.e., an administrator or operator). To facilitate local access, the system server 200 includes an interactive user interface 210. The health tracking application 218, and may collect data from and store data to the memory 206. In at least one embodiment, the user interface 210 may suitably include an LCD touch screen or the like, a mouse or other pointing device, a keyboard or other keypad, speakers, and a microphone, as will be recognized by those of ordinary skill in the art. Accordingly, the user interface 210 is configured to provide an administrator or other authorized user with access to the memory 206 and allow the authorized user to amend, manipulate and display information contained within the memory.

As mentioned above, the memory 206 includes various programs and other instructions that may be executed by the processor circuitry/logic 204. In particular, the memory 206 of the system server 200 of FIG. 2 includes the health tracking program 218 (which may also be referred to herein as a "health tracking application" and/or the "network-side health tracking application"). The health tracking program 218 is configured to cause the system server 200 to enable a user to obtain nutritional data related to any of various consumables. Execution of the health tracking application 218 by the processor circuitry/logic 204 results in signals being sent to and received from the user interface 210 and the communications module 212 (for further delivery to a user device such as a health tracking device 110), in order to allow the user receive and update various aspects of the consumable records 224. The network-side health tracking application 218 is configured to provide various graphical views and screen arrangements to be displayed to a user on a health tracking device 110.

The user data 222 includes at least user profiles 230 and corresponding consumable logs 232, and activity logs 234. The user profiles 230 include profile data for each user of the health tracking system 100. Each user profile includes demographic information for the users, such as name, age, gender, height, weight, performance or activity level (e.g., beginner, intermediate, professional, sedentary, active, etc.) and/or other information relating to the user. In at least one embodiment, the consumable logs 232 include a consumable diary/log for each user (discussed in greater detail below). The performance level may be determined based on an amount and/or frequency of recorded activity. For example, users who log several hours of workouts per week may be deemed "active" while those that record less than two hours per week are deemed "sedentary", etc. In other embodiments, rather than a systematic or automatic determination of the user's activity or performance level, the user him/herself may enter the information based on a subjective view of his/her lifestyle. Each user profile 230 may also include one or more goals. The user's goals may be provided as any number of different types of goals, such as activity goals, dietary goals, weight-loss goals, or any of various other health-related goals. The user goals may be long-term or short term goals. For example, one user goal may be to lose twenty-five pounds within a year. Another user goal may be to limit calorie consumption at breakfast to 400 total calories per day. Also, the user goals may also be general or specific goals. An example of a specific user goal is to limit calorie consumption to 1500 calories per day, 500 calories per meal, or some other calorie value related to a specific period of time (e.g., a week, a day, or a morning, noon, or evening meal). Other examples may rely instead on meeting specific macronutrient goals, such as at least 100 g of protein per day, etc. An example of a general user goal is to have a "healthy-lifestyle," "vegetarian diet," or "muscle building" as a goal.

In at least one embodiment, the consumable logs 232 include a consumable diary/log for each user. The consumable diary/log allows the user to track items that are consumed by the user over a day, a period of days, etc., and any nutritional data associated with each item consumed. For example, the consumable diary/log may allow the user to enter, via a user device 110, a particular item that is or was consumed by the user and have data relating thereto stored so that the user may keep track of e.g., the associated calories, macronutrients, micronutrients, sugar, fiber, and/or any of various other nutritional data associated with the consumables entered by the user in the consumable diary/log. Each consumable entered into the consumable diary/log may be associated with a particular day and, even further, to a particular meal within that day. In some embodiments, the user data 222 further includes various activity and fitness data collected by sensors (not shown) associated with the health tracking devices 110.

The activity logs 234 include various activity and fitness data which is either manually entered or automatically collected by sensors (not shown) associated with the health tracking devices 110. The sensors may comprise, for example, GPS devices, accelerometers, heart rate monitors, temperature sensors, etc. The activity logs 234 may indicate any of various activity-related parameters such as step count, heart rate, distance travelled, calories burned, etc. The activity logs 234 provide a diary/log of health and fitness data for a user that extends over some period of time, such as days, week, months, years, etc.

In an alternative embodiment, the foregoing profile data may be stored at a storage entity separate from, yet in communication with, the server 200. For example, a centralized server may be provided which is configured to store all data relating to an individual user in one storage area (including workout data, nutrition/consumption data, profile data, etc.). With continued reference to FIG. 2, in addition to the user data 222, the data stored in the memory 206 also includes consumable records 224, operational records 226, and graphics 228. A plurality of consumable records 224 are stored in the database 220. As discussed above, the phrase "consumable record" refers to a database record that relates to a particular consumable item. In the disclosed embodiment, each of the consumable records includes a number of fields including, for example, a name for the consumable item, summary information about the consumable item, and detailed nutritional information about the consumable item. Detailed information about a consumable item may include one or more of: serving size, calories, ingredients, or any other nutritional information about the consumable. For example, the nutritional information may include information that may be provided on USDA food labels or state-regulated food labels (e.g., vitamin and mineral content, fat content, cholesterol content, protein content, sugar content, carbohydrate content, fiber content, organic contents, etc.). The summary information about the consumable item may include a subset of the detailed information listed above. For example, the summary information about the consumable may only include serving size and calorie information. The various fields of each consumable record may be populated by data from any user or third party data providers. Therefore, it will be recognized that in at least some embodiments, consumable records 224 may have been entered by any of various sources including an administrator or operator of the health tracking system 100, commercial food providers (e.g., food distributors, restaurant owners, etc.), and/or users of the health tracking system 100.

The operational records 226 include current and historical data stored by the system server 200 in association with operation of the system server 200, execution of the health tracking application 218, and/or manipulation of data 220 within the memory 206. For example, the operational records 226 may include information concerning amendments made to any of various consumable records 224. The operational records 226 may also include other information related to the control and operation of the system server 200, including statistical, logging, licensing, and historical information.

In one embodiment, graphical views 228 are provided at the server 200 which are pushed to the health tracking device 110 for display thereat of various screen arrangements, as shown in FIG. 1.

While the system server 200 has been explained in the foregoing embodiment as housing the health tracking program 218 and the various records and databases in the memory 206, it will be recognized that in other embodiments these components may be retained in one or more other remote locations in communication with the health tracking system 100. For example, in at least one embodiment, the consumable records 224 may be data retained by a database separate from the system server 200. Alternatively, the consumable records 224 or certain fields of the consumable records 224 are received from a third party database. In such embodiments, the health tracking application may utilize any number of application programming interfaces (APIs) to access the data in the third party databases and incorporate such information for use in the health tracking application 218, without local storage thereof and/or utilizing only temporary storage. Accordingly, it will be recognized that the description of the system server 200 of FIG. 2 is but one exemplary embodiment of a data processing system that may be utilized by the health tracking system 100.

A computer program product implementing an embodiment disclosed herein may therefore comprise one or more computer-readable storage media storing computer instructions executable by a processor to provide an embodiment of a system or perform an embodiment of a method disclosed herein. Computer instructions (e.g., the health tracking application 218) may be provided by lines of code in any of various languages as will be recognized by those of ordinary skill in the art. A "non-transitory computer-readable medium" may be any type of data storage medium that may store computer instructions, including, but not limited to a memory card, ROM, RAM, write-capable memories, read-only memories, hard drives, discs, flash memory, or any of various other computer-readable medium.

Health Tracking Devices

With reference again to FIG. 1, the health tracking devices 110 may be provided in any of various forms. Examples of a health tracking devices 110 configured for use with the health tracking system 100 include a smartphone 110A, a laptop computer 110B, and a desktop computer 110C, as shown in FIG. 1, as well as various other electronic devices. Accordingly, it will be recognized that the health tracking devices 110 may comprise portable electronic devices such as the smartphone 110A or the laptop computer 110B, or stationary electronic devices such as the desktop computer 110C. Other examples of health tracking devices include, handheld or tablet computers, smart watches, portable media players, other wearable devices, or any of various other health tracking devices configured to receive entry of consumables (not shown) and/or comprising sensors to obtain health related data.

In one embodiment, data obtained at one device 110 may be provided to other devices 110 associated with the same user. For example, data entered at the smart phone 110A may be provided to the desktop computer 110C and/or the laptop computer 110B for storage thereat. Alternatively, the data may be stored at a single network storage apparatus (not shown) having a dedicated portion of storage for records relating to the user and accessible by all of the user's devices 110.

Figure 3:
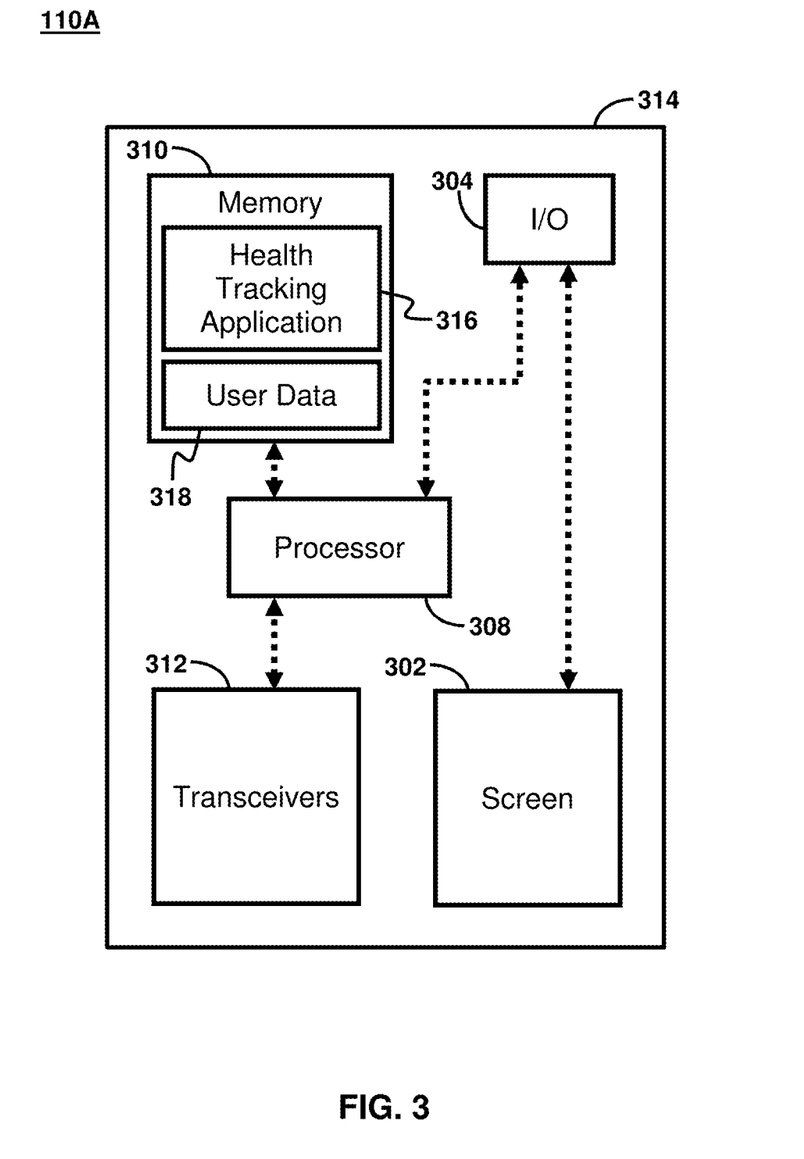
FIG. 3 is a block diagram illustrating an exemplary smartphone of the health tracking system of FIG. 1.

With reference now to FIG. 3, in at least one embodiment the health tracking device 110 comprises a smartphone 110A. The smartphone 110A includes a display screen 302, an input/output (I/O) interface 304, a processor 308, a memory 310, and one or more transceivers 312. The smartphone 110A also includes a protective outer shell or housing 414 designed to retain and protect the electronic components positioned within the housing 414. The smartphone 110A also includes a rechargeable battery (not shown) configured to power the display screen 302, processor 308, transceivers 312 and various other the electronic components within the smartphone 110A.

The display screen 302 of the smartphone 110A may be an LED screen or any of various other screens appropriate for the personal electronic device. The I/O interface 304 of the smartphone 110A includes software and hardware configured to facilitate communications with the user. The I/O interface 304 is in communication with the display screen 302 and is configured to visually display graphics, text, and other data to the user via the display screen 302. As will be recognized by those of ordinary skill in the art, the components of the health tracking device 110 may vary depending on the type of display device used. Alternative health tracking devices, such as the laptop 110B and the desktop 110C, may include much of the same functionality and components as the smartphone 110A shown in FIG. 3 and/or may include others not listed.

The processor 308 of the smartphone 110A may be any of various processors as will be recognized by those of ordinary skill in the art. The processor 308 is in communication with the I/O interface 304, the memory 310, and the transceivers 312, and is configured to deliver data to and receive data from each of these components. The memory 310 is configured to store information, including data and instructions for execution by the processor 308. It will be recognized by those of ordinary skill in the art that a "processor" includes any hardware system, hardware mechanism or hardware component that processes data, signals or other information. A processor may include a system with a central processing unit, multiple processing units, dedicated circuitry for achieving functionality, or other systems.

The transceivers 312 may be any of various devices configured for communication with other electronic devices, including the ability to send communication signals and receive communication signals. The transceivers 312 may include different types of transceivers configured to communicate with different networks and systems. Such transceivers are well known and will be recognized by those of ordinary skill in the art. In some embodiments, the transceivers 312 include at least one transceiver configured to allow the smartphone 110A to perform wireless communications with the cell towers 115 of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceivers 312 include at least one transceiver configured to allow the smartphone 110A to communicate with any of various local area networks using Wi-Fi, Bluetooth® or any of various other communications schemes.

The memory 310 includes both program instructions and data. For example, the memory 310 may include program instructions for a graphical user interface configured to provide a client-side health tracking application 316. The memory 310 may further be configured to store certain user data 318, including user profile data such as, e.g., user gender, height, weight, user identifier, password, etc. Additionally, user data such as activity and other health related data (e.g., data collected from one or more sensors and/or manually entered) may be stored. The processor 308 is configured to read the program instructions from the memory 310 and execute the program instructions to provide the health tracking application 316 to the user so for the purpose of performing health and fitness related tasks for the user, including displaying, modifying, and analyzing the user data 318.

In at least one embodiment, the user data 318 includes a plurality of consumable records which serves as a log of consumables that have been consumed by the user for the purpose of caloric and nutritional tracking. That is to say, the client-side health tracking application 316 is configured to display a searchable list of consumable items (including certain information from a record associated thereto) and enable the user to select individual ones thereof (each associated to individual ones of a plurality of consumable records accessed via the network 120). The selected items correspond to consumables that the user has consumed and accordingly information relating thereto is stored at the client-side for the purpose of logging in this embodiment. In another alternative, such log may be stored remote from the device and/or only kept at the device for a transitory period.

The memory 310 that retains the data and instructions may be of any type of device capable of storing information accessible by the processor, such as a memory card, ROM, RAM, write-capable memories, read-only memories, hard drives, discs, flash memory, or any of various other computer-readable medium serving as data storage devices as will be recognized by those of ordinary skill in the art. Portions of the system and methods described herein may be implemented in suitable software code that may reside within the memory as software or firmware. Alternatively, or in addition, the software (such as e.g., the client-side health tracking application 316) may be downloaded from a network location, such as via the Internet.

Method for Logging Cheat Day Consumable Items

Methods for operating the health tracking system 100 are described below. In particular, a method for tracking consumable items that are purposefully omitted in calculation of a user's progress toward his/her goals is provided. In the description of the methods, statements that a method is performing some task or function refers to a controller or general purpose processor executing programmed instructions stored in non-transitory computer readable storage media operatively connected to the controller or processor to manipulate data or to operate one or more components in the health tracking system 100 to perform the task or function. Particularly, the processor circuitry/logic 204 of the system server 200 and/or the processor 308 of the smartphone 110A above may be such a controller or processor. Alternatively, the controller may be implemented with more than one processor and associated circuitry and components, each of which is configured to form one or more tasks or functions described herein. Additionally, the steps of the methods may be performed in any feasible chronological order, regardless of the order shown in the figures or the order in which the steps are described.

Figure 4:
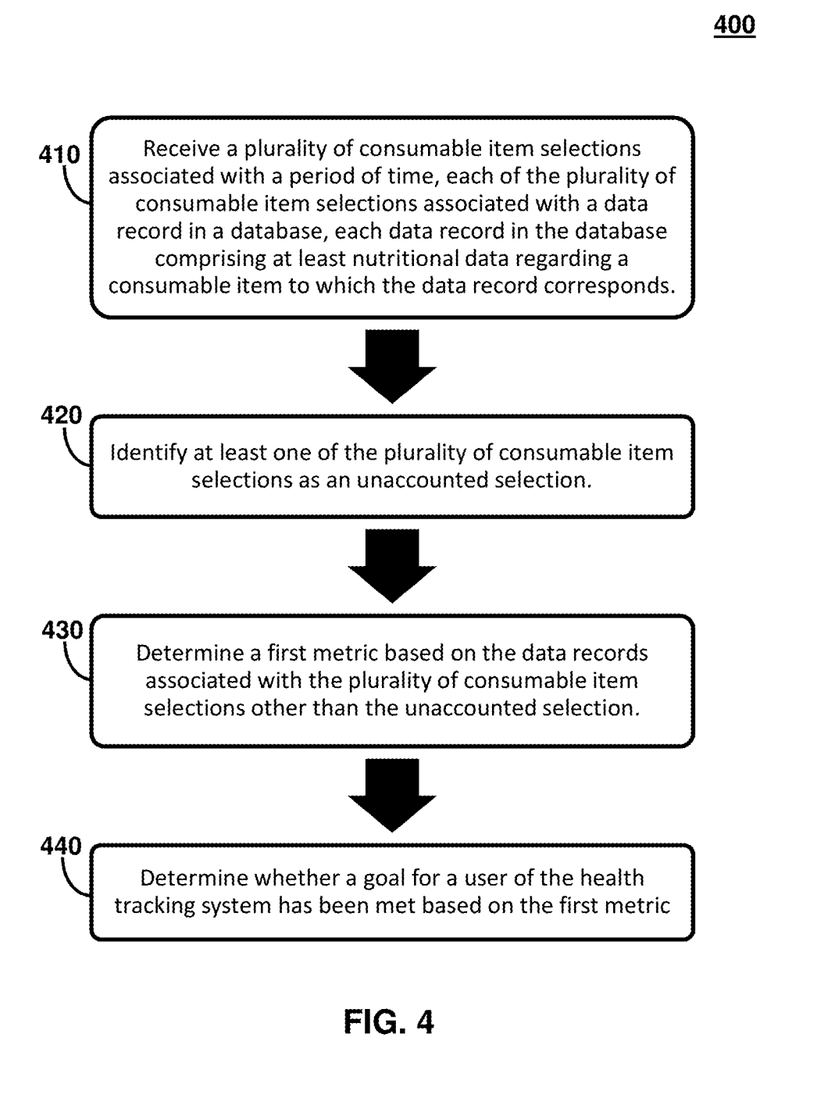
FIG. 4 is a block diagram illustrating an exemplary method for enabling tracking of one or more consumable items associated with cheat meal or cheat day.

FIG. 4 shows a method 400 for tracking consumables that are purposefully omitted in association with user goals and thus associated with cheat meal and/or a cheat day. First, a plurality of consumable item selections are received. In one embodiment, each of the selections is associated with a period of time, each of the plurality of consumable item selections is associated with a data record in a database, and each data record in the database comprises at least nutritional data regarding a consumable item to which the data record corresponds (block 410). Particularly, with respect to the embodiments described in detail herein, the processor 308 of the smartphone 110A is configured to receive the plurality of consumable item selections from a user via the I/O interface 304. Alternatively, in another embodiment, the processing circuitry/logic 204 of the system server 200 is configured to receive the plurality of consumable item selections from the smartphone 110A or other health tracking device 110 of associated with a user.

The plurality of consumable item selections embodies a subset of the entries in the user's consumable log/diary that are associated with the particular period of time to which they are associated. In particular, the plurality of consumable item selections may comprise the consumables items that the user has consumed and logged for a particular week, for a particular day, and/or for a particular meal on a particular day. Each consumable item selection is associated with a particular consumable record in the consumable records database 224 of the system server 200.

The method 400 continues with a step of identifying at least one of the plurality of consumable item selections to be purposefully omitted or unaccounted (block 420). Particularly, with respect to the embodiments described in detail herein, the processor 308 of the smartphone 110A and/or the processing circuitry/logic 204 of the system server 200 is configured to identify one or more of the consumable item selections as being a consumable item selection that will be purposefully unaccounted for in association with user goals, and thus associated with a cheat meal and/or cheat day. In one embodiment, the processor 308 of the smartphone 110A is configured to receive an input from the user via the I/O interface 304 indicating which of the consumable item selections are to be flagged, tagged, labeled, or otherwise identified as consumable item that is to be purposefully omitted from e.g., a daily goals calculation. In one embodiment, the processing circuitry/logic 204 of the system server 200 is configured receive an input from the smartphone 110A or other health tracking device 110 indicating which of the consumable item selections are to be flagged as a mere placeholder (i.e., displayed but not counted toward a daily goal total, etc.). The processor 308 of the smartphone 110A and/or the processing circuitry/logic 204 of the system server 200 is configured to flag one or more of the consumable item selections based on the received input from the user.

Figure 5:
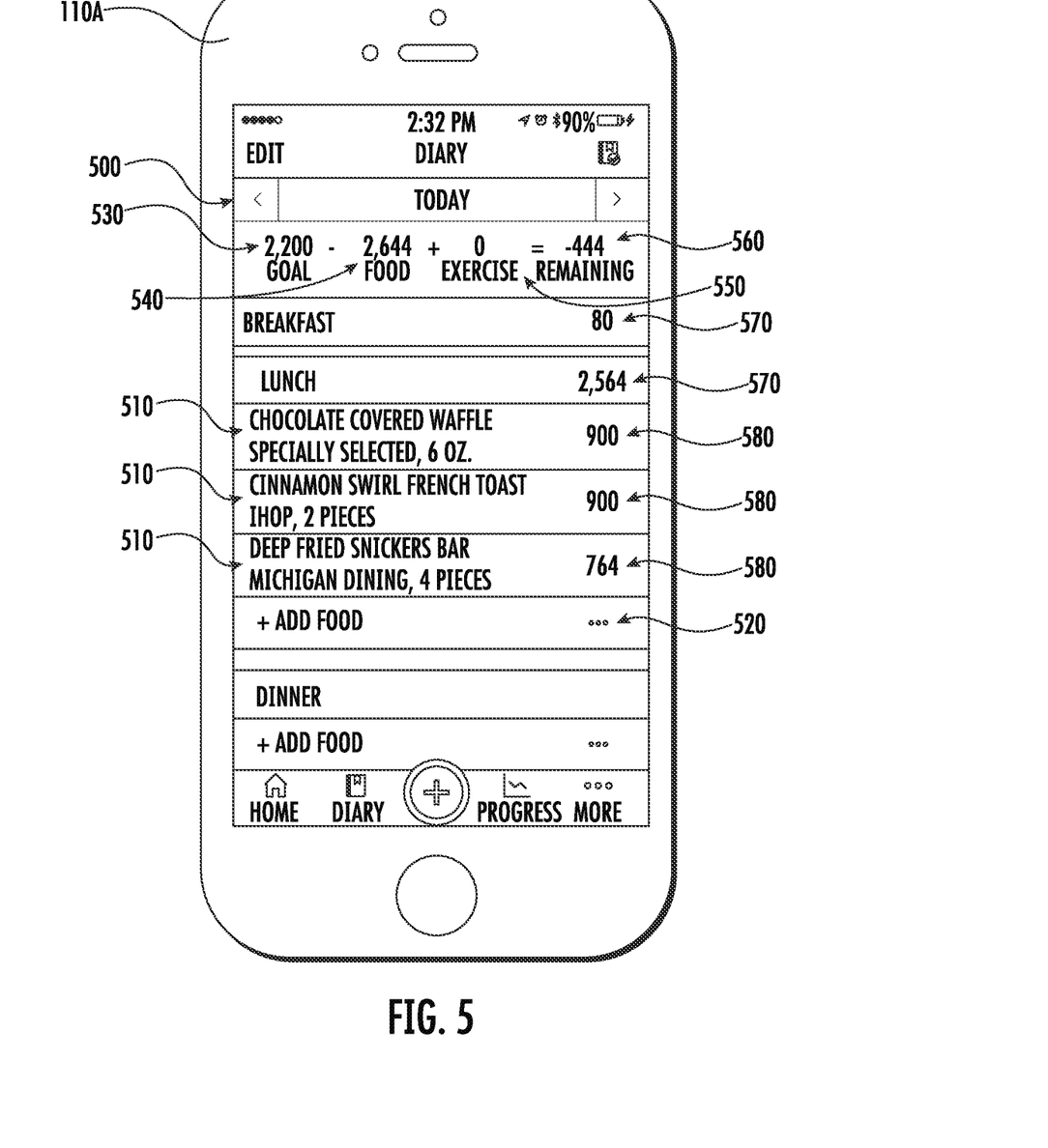
FIG. 5 is a representation of an exemplary user interface for identifying a consumable item selection as being associated with a cheat meal or cheat day.

With reference to FIG. 5, an exemplary user interface for enabling a user to log one or more consumable items using the smartphone 110A without having those items used in a nutrition and/or calorie count for the day is briefly described to further aid in the understanding of the disclosure. Particularly, when a user opens the client-side health tracking application 316 of the smartphone 110A, he or she is provided with the illustrated graphical user interface (GUI) 500 that is displayed on the screen 302. (Alternatively, the GUI may be displayed on any computerized device associated with the user.). The GUI 500 shows consumable item selections 510 that the user has selected to be logged in his or her consumable log/diary. As shown, the user has logged some particularly unhealthy consumable items for his or her lunch, including "Chocolate covered waffle", "Cinnamon Swirl French Toast", and "Deep Fried Snickers Bar"). The total calories associated with these consumable items is 2564 total calories (i.e., 900+900+764=2564), which is in excess of the user's total daily goal of 2200 calories. Accordingly, the user may wish to mark one or more of these consumable item selections 510 as being associated with a cheat meal and/or cheat day and therefore omitted from calculation of the day's calories and/or other nutrients.

Figure 6:
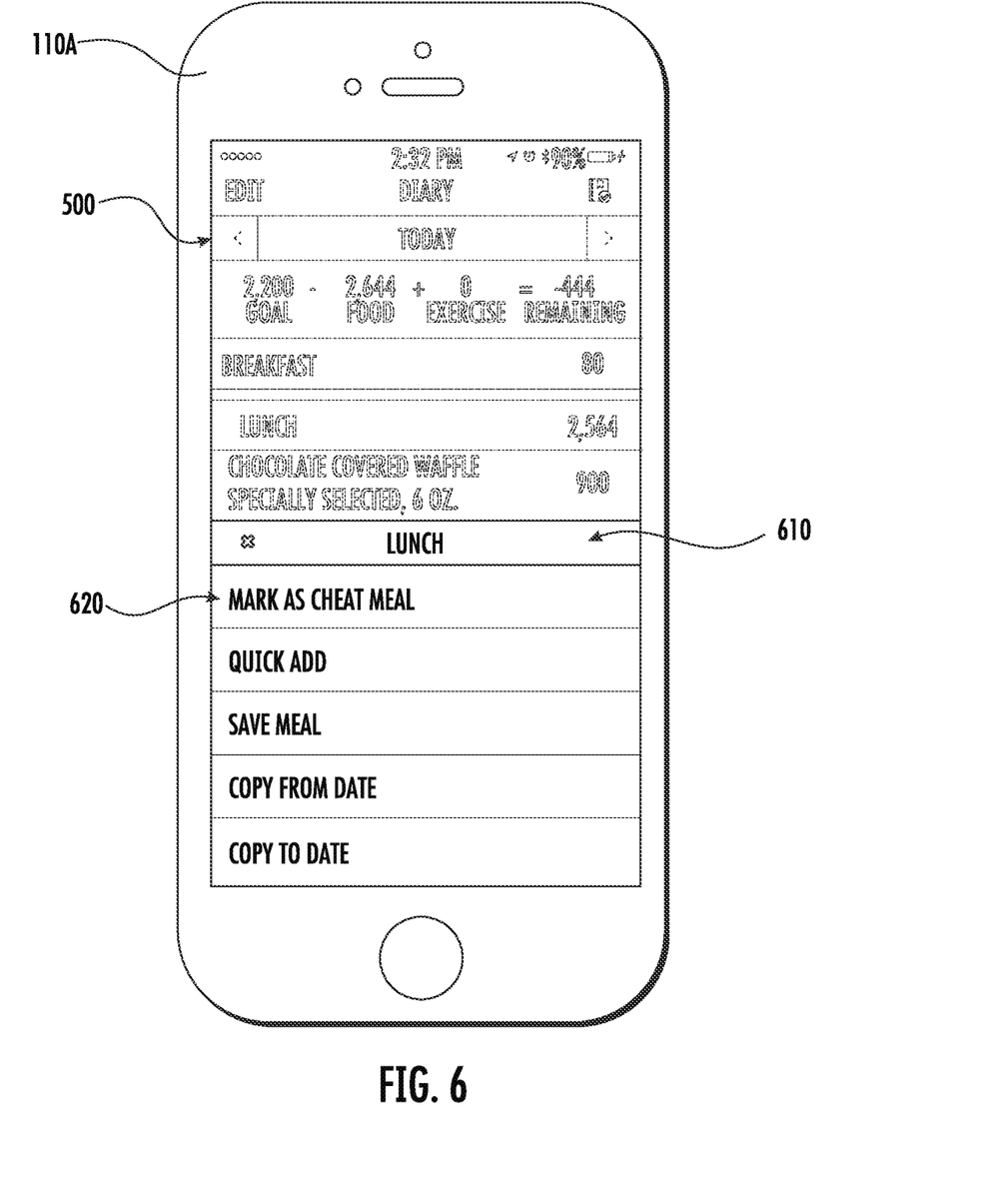
FIG. 6 is a further representation of an exemplary user interface for identifying a consumable item selection as being associated with a cheat meal or cheat day.

In the given example, in order to mark one or more of the consumed items 510 as a cheat meal, the user presses a menu button 520 (shown as an ellipses " . . . " above the word "More"). When the menu button 520 is pressed, one or more menu options are provided for performing various operations. With reference to FIG. 6, an exemplary menu 610 is shown. The menu 610 provides multiple options for performing various operations with respect to the selected consumable item (i.e., "Chocolate covered waffle," "Cinnamon Swirl French Toast," or "Deep Fried Snickers Bar") or the selected meal (i.e. "Lunch"). In this case, the "Lunch" meal has been selected by the user, so the menu 610 includes an option 620 for marking all consumable item selections 510 in the respective meal to not be counted toward a calorie and/or nutrition goal, i.e., associated with a cheat meal (shown in the example with the identifier: "Mark As Cheat Meal"). In one variant, the caloric and/or nutrition values for the selected cheat items are temporarily set to zero. The zero values may be maintained locally and separate from the data records such as at e.g., the user device 110 and/or the server 200 in order to not impact or alter the actual item records stored at the database 220.

When the option 620 is selected by the user, all the consumable item selections 510 logged in association with the respective meal (i.e., "Lunch") are flagged as being associated with a cheat meal. It is noted that the menu 610 is merely exemplary and that other designs and processes for marking consumable items as being associated with a cheat meal are possible. For example, it will be recognized that if the user selects only a single consumable item selection 510, the menu 610 will include an option for marking only that consumable item selection 510 as being an unaccounted selection associated with a cheat meal or cheat day. Additionally, entire days or weeks can be mark as cheat days or cheat weeks.

In a further embodiment, the user may be given an option to select a certain meal, day, and/or week during the month as being a scheduled cheat meal, day, week, etc. In this manner, the user may be relieved of having to individually mark the days, meals, etc. which are not to be counted toward a calorie and/or nutrition goal when he/she follows a particular schedule for such cheats.

Returning to FIG. 4, following the identification of one or more selections of items which are not to count toward the users calorie and/or nutrition targets (i.e., "cheat selections") in block 420, the method 400 continues in block 430 wherein a first metric is determined based on the data records associated with the plurality of consumable item selections other than those which were selected as not to be counted toward the user's calorie and/or nutrition goal or target. Particularly, with respect to the embodiments described in detail herein, the processor 308 of the smartphone 110A and/or the processing circuitry/logic 204 of the system server 200 is configured to calculate a value for a metric based the data records associated with the consumable item selections (excluding the items identified to be cheat meals). In several embodiments, the metric is related to the nutritional contents of the consumable item selections and is calculated based on nutritional data in the consumable records associated with the consumable item selections that are not flagged to be purposefully unaccounted (i.e., the non-flagged consumable items are accounted consumable items and the metric is calculated based only on these accounted consumable items).

In one embodiment, the metric is an amount of calories consumed by the user for a particular meal, a particular day, or a particular week. The processor 308 of the smartphone 110A and/or the processing circuitry/logic 204 of the system server 200 is configured to calculate the amount of calories consumed by the user based on the caloric data in the consumable records associated with the consumable item selections that are not flagged as cheat items. More particularly, the amount of calories consumed by the user is calculated as a sum of the caloric content of each of the consumable item selections that is not flagged as being purposefully omitted.

In one embodiment, the metric which is calculated comprises an amount of a macronutrient consumed by the user for a particular meal, a particular day, or a particular week (i.e. an amount of protein, fat, or carbohydrates consumed). The processor 308 of the smartphone 110A and/or the processing circuitry/logic 204 of the system server 200 is configured to calculate the amount of the macronutrient consumed by the user based on the data stored in the consumable records associated with the consumable item selections that are not flagged to be unaccounted consumable items. More particularly, the amount of the macronutrient consumed by the user is calculated as a sum of the macronutrient content of each of the consumable item selections (excluding those items selected to be purposefully omitted).

In several embodiments, the metric is related to a health goal for the user. Particularly, the user may have a goal for the metric that he or she aims to meet. In this case, the method 400 continues with a step of determining whether a goal for a user of the health tracking system has been met based on the first metric (440). Particularly, with respect to the embodiments described in detail herein, the processor 308 of the smartphone 110A and/or the processing circuitry/logic 204 of the system server 200 is configured to determine whether a goal relating to the metric has been met.

In one embodiment, the goal includes a limited daily calorie intake. The processor 308 of the smartphone 110A and/or the processing circuitry/logic 204 of the system server 200 is configured to compare the actual amount of calories consumed by the user with the target amount of calories consumed to determine if the goal was met. For example, if a user's health goal is to lose weight, then the goal is met if the actual amount of calories consumed is less than or equal to the target amount of calories consumed. Conversely, the user's health goal is to gain weight, then the goal is met if the actual amount of calories consumed is greater than or equal to the target amount of calories consumed.

In other embodiments, the goal includes a target amount of a macronutrient to consume for a particular day. The processor 308 of the smartphone 110A and/or the processing circuitry/logic 204 of the system server 200 is configured to compare the actual amount of the macronutrient consumed by the user with the target amount of the macronutrient consumed to determine if the goal was met. For example, if a user's health goal is to build or maintain lean muscle mass, then he or she may have target amount of protein to consume each day in conjunction with a strength-training program. Accordingly, the goal would be met if the actual amount of protein consumed is greater than or equal to the target amount of protein consumed. As another example, if a user's health goal is to eat a low-carbohydrate diet for weight loss, then he or she may have a target amount of carbohydrates to consume each day. Accordingly, the goal would be met if the actual amount of carbohydrates consumed is less than or equal to the target amount of carbohydrates.

In some embodiments, the metric and the determination of whether the goal has been met are displayed on the health tracking device 110. Particularly, in one embodiment, the processor 308 of the smartphone 110A is configured to operate the I/O interface 304 to display the metric and/or the determination of whether the health goal has been met on the screen 302. In one embodiment, the processing circuitry/logic 204 of the system server 200 is configured transmit the metric and/or the determination of whether the health goal has been met to the smartphone 110A for display on the screen 302.

Returning to FIG. 5, an exemplary display of the metric and the determination of whether the health goal has been met is shown. Particularly, the GUI 500 shows values for target daily calories 530 (i.e., 2,200 calories), actual daily calories 540 (i.e., 2,644 calories), and calories earned from exercise 550 (i.e., 0 calories). The GUI 500 shows a value for calories remaining 560 (i.e., −444 calories), which is determined by subtracting the actual daily calories 540 from the target daily calories 530 and adding the calories earned from exercise 550. Additionally, the GUI 500 shows values for meal-specific calorie subtotals 570 (i.e., 80 calories for breakfast and 2,564 calories for lunch) and consumable item-specific subtotals 580 for each consumable item selection 510 that is logged (i.e., 900 calories for 6 Oz. of "Chocolate covered waffle", 900 calories for 2 pieces of "Cinnamon Swirl French Toast", and 764 calories for 4 pieces of "Deep Fried Snickers Bar").

As shown in FIG. 5, the consumable item selections 510 have not yet been flagged as being as being associated with a cheat meal. Accordingly, values for the consumable item-specific subtotals 580 are shown and reflected in the values for the lunch calorie subtotal 570 and actual calories consumed 540. The calories from the consumable item selections 510 for lunch are also reflected in the value for calories remaining 560. Since the goal of a 2,200 calorie limit for the day has not been met (and has been exceeded at this point), the value for calories remaining 560 is negative (i.e., "−444") and is shown in red to indicate that the goal has been exceeded.

Figure 7:
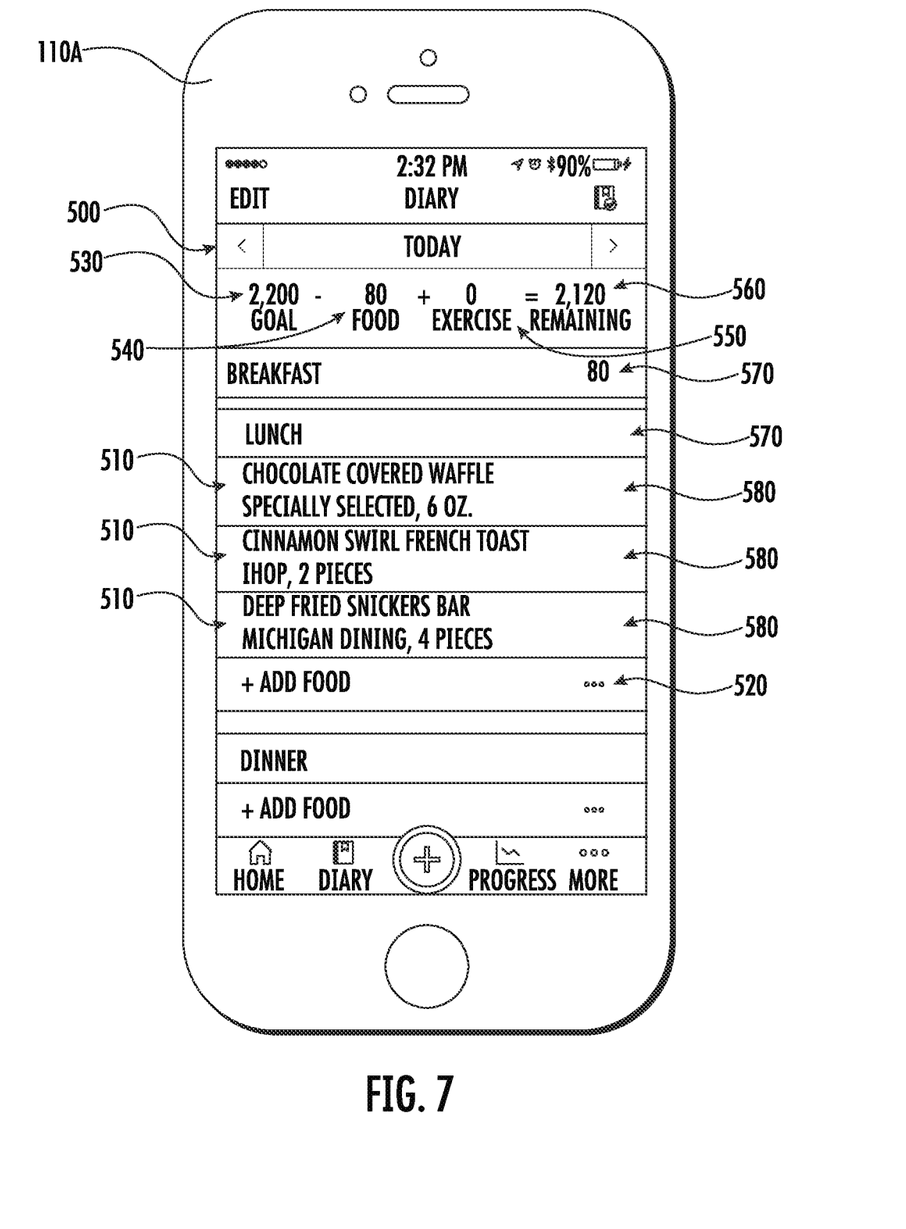
FIG. 7 is a representation of an exemplary user interface in which caloric information is hidden and/or ignored for consumable item selections associated with a cheat meal or cheat day.

As described above, the user can flag the lunch consumable item selections 510 as being associated with a cheat meal. FIG. 7 shows the GUI 500 after the lunch consumable item selections 510 have been flagged as being associated with a cheat meal. Since the lunch consumable item selection 510 have are flagged as being associated with a cheat meal, the respective consumable item-specific calorie subtotals 580 are hidden. Additionally, since every consumable item selection 510 for lunch has been flagged as being associated with a cheat meal, the lunch-specific calorie subtotal 570 is also hidden. However, the breakfast-specific calorie subtotal 570 is not hidden because the respective lunch items have not been flagged and the items are therefore to be counted. Additionally, the caloric content of each of the consumable item selections 510 that are flagged consumable items which are to be unaccounted is not reflected in the value for actual daily calories 540 (e.g. only shows the 80 calories associated with breakfast). Finally, the value for calories remaining 560 is positive (i.e., 2,120 calories remaining, reflecting only the 80 calories associated with breakfast) and shown in green to indicate that the goal not been exceeded. In this way, the user can enjoy his or her cheat meal without the embarrassment and guilt caused by the meal being reflected against his or her health goals for the day.

In some embodiments, the GUI 500 also enables a user to view the hidden cheat day or cheat meal information. In one embodiment, the user can access a separate menu or view in the GUI 500 (not shown) that shows the hidden calorie information associated with consumable items that are flagged as being associated with a cheat meal or cheat day. In one embodiment, a user can 'long press' or 'deep press' on one of the consumable items or one of meals to temporarily reveal the hidden calorie totals.

In one embodiment, the consumable item selections that are flagged as being associated with a cheat meal or cheat day can be used to generate recommendations for the user. Particularly, the processor 308 of the smartphone 110A and/or the processing circuitry/logic 204 of the system server 200 is configured to generate a recommendation for a user based on which of the plurality of consumable item selections are flagged as being associated with a cheat meal or cheat day. In one embodiment, the recommendation is a recommended consumable item for the user that is a healthier but similar alternative to the consumable item selections that are flagged as being associated with a cheat meal or cheat day. These recommendations can be displayed to the user using the GUI 500, or the like.

The methods discussed herein may be accomplished with the assistance of a computer program, such as the network and/or client side health tracking programs described above. The above described system and method solves a technological problem common in industry practice related to effective and efficient entry and processing of data records related to consumable items and presentation of associated data to the user. Moreover, the above-described system and method improves the functioning of the computer/device and particularly health tracking devices by allowing some consumable items to be unaccounted for when determining metrics associated with user goals. Additionally, the above-described system and method improves the functioning of the computer/device and particularly health tracking devices by allowing health data to be effectively communicated to the user along with a graphical user interface that presents options related to purposefully unaccounted data records to the user.

Portions of the system and methods described herein may be implemented using one or more programs or suitable software code, such as the network and/or client-side health tracking applications, described above, each of which may reside within the memory of the respective computing devices as software or firmware. Such programs and code may be stored in the memory and executed by the processor of the display device or a system server or other computer in communication with the display device. A computer program product implementing an embodiment disclosed herein may therefore comprise one or more computer-readable storage media storing computer instructions translatable by processing circuitry/logic, a CPU, or other data processing device to provide an embodiment of a system or perform an embodiment of a method disclosed herein. Computer instructions may be provided by lines of code in any of various languages as will be recognized by those of ordinary skill in the art.

A "computer-readable medium" may be any type of data storage medium that can store computer instructions and/or data, including, read-only memory (ROM), random access memory (RAM), hard disks (HD), data cartridges, data backup magnetic tapes, floppy diskettes, flash memory, optical data storage, CD-ROMs, or the like. The computer readable medium can be, by way of example, only but not by limitation, an electronic, magnetic, optical, electromagnetic, infrared, or semiconductor system, apparatus, system, device, or computer memory. The computer readable medium may include multiple computer readable media storing computer executable instructions, such as in a distributed system or instructions stored across an array. A "non-transient computer-readable medium" may be any type of data storage medium that can store computer instructions, including, but not limited to the memory devices discussed above.

The above described system and method solves a technological problem common in industry practice of procuring receipt of consumption data from the user and assisting users in evaluating user goals or other metrics. Moreover, the above-described system and method improves the functioning of the computer device by enabling users to enter consumption data and also identify consumption data that should be purposefully omitted in association with the calculation of user goals or other metrics. In the foregoing description, various operations may be described as multiple discrete actions or operations in turn, in a manner that may be helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

The foregoing detailed description of one or more exemplary embodiments of the health tracking system has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed exemplary embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the exemplary embodiments contained herein.

What is claimed is:

1. A method of operating a health tracking system, the method comprising:

receiving, from a health tracking device of a user of the health tracking system, a plurality of consumable item selections associated with a period of time and a meal during the period of time, each of the plurality of consumable item selections associated with a data record in a database, each data record in the database comprising nutritional data regarding a consumable item to which the data record corresponds, wherein each of the plurality of consumable item selections is indicative of the user having consumed the consumable item associated with the consumable item selection during the period of time;

displaying the plurality of consumable item selections to the user on a display screen of the health tracking device, each of the plurality of consumable item selections displayed in association with a meal description and the period of time on the display screen;

calculating a first metric based on the nutritional data regarding the plurality of consumable item selections associated with the period of time, and displaying the first metric on the display screen along with the period of time;

after displaying the plurality of consumable item selections and calculating the first metric, displaying on the display screen an option to remove consumable item selections associated with one of the meal descriptions from said first metric;

in response to selection of the option to remove, identifying consumable item selections associated with said one of the meal descriptions to be purposefully omitted from the first metric;

re-calculating the first metric based on the nutritional data regarding the plurality of consumable item selections, the re-calculation comprising purposeful omission of the nutritional data of the identified consumable item selections associated with said one of the meal descriptions to be purposefully omitted;

after re-calculating the first metric, displaying the first metric on the display screen along with the period of time and the plurality of consumable item selections associated with the period of time, wherein said plurality of consumable item selections displayed include the identified consumable item selections associated with said one of the meal descriptions to be purposefully omitted;

generating recommended one or more additional consumable items based at least in part on an association of said one or more additional consumable items with said consumable item selections to be purposefully omitted, wherein the recommended additional consumable items are determined to be associated with healthier nutritional data than the identified ones of the consumable item selections; and displaying said recommended additional consumable item selections on the display screen of the health tracking device.

2. The method of claim 1, further comprising:
determining whether a goal for a user of the health tracking system has been met by comparing the calculated first metric to a threshold value therefor.

3. The method of claim 2 wherein said calculated first metric is displayed on the display screen in a first color indicative of said user not achieving said goal, and wherein said recalculated first metric is displayed on the display screen in a second color indicative of said user achieving said goal.

4. The method of claim 1, wherein:
the nutritional data comprises a calorie amount;
the first metric comprises a total amount of calories consumed by a user;
the act of calculating the first metric further comprises adding the caloric amount of each of the plurality of consumable item selections; and
the act of recalculating the first metric comprises purposeful omission of the caloric amount of the identified at least one of the plurality of consumable items.

5. The method of claim 1, wherein:
the nutritional data comprises a macronutrient amount;
the first metric comprises a total amount of the macronutrient consumed by a user;
the act of calculating the first metric further comprises adding the macronutrient amount of each of the plurality of consumable item selections; and the act of recalculating the first metric comprises purposeful omission of the macronutrient amount of the identified at least one of the plurality of consumable items.

6. The method of claim 1, wherein the period of time comprises at least one of: a particular week, a particular day, and period associated to a particular meal on a particular day.

7. The method of claim 1, wherein the act of identifying further comprises:
receiving at the health tracking device, an input from a user selecting the at least one of the plurality of consumable item selections to be purposefully omitted; and
flagging the selected at least one of the plurality of consumable item selections based on the received input.

8. The method of claim 1 wherein the recommended alternative consumable item selections are determined to be associated with healthier nutritional data based at least on a calorie total for the recommended alternative consumable item selections being less than said identified ones of the consumable item selections.

9. A method of operating a health tracking system, the method comprising:
receiving, from a health tracking device of a user of the health tracking system, a plurality of consumable item selections associated with a period of time, each of the plurality of consumable item selections associated with a data record in a database, each data record in the database comprising nutritional data regarding a consumable item to which the data record corresponds, wherein each of the plurality of consumable item selections is indicative of the user having consumed the consumable item associated with the consumable item selection during the period of time;
displaying the plurality of consumable item selections to the user on a display screen of the health tracking device, each of the plurality of consumable item selections displayed in association with the period of time on the display screen;
calculating a first metric based on the nutritional data regarding the plurality of consumable item selections associated with the period of time, and displaying the first metric on the display screen;
after displaying the first metric, displaying an option to remove from the first metric nutritional data associated with identified ones of the plurality of consumable item selections;
in response to selection of the option to remove, recalculating the first metric based on the nutritional data regarding the plurality of consumable item selections, the recalculation comprising purposeful omission of the nutritional data of the identified ones of the plurality of consumable item selections; and
in response to selection of the option to remove, generating recommended alternative consumable item selections for the identified ones of the consumable item selections, wherein the recommended alternative consumable item selections are determined to be associated with healthier nutritional data than the identified ones of the consumable item selections; and
displaying said recommended alternative consumable item selections on the display screen of the health tracking device.

10. The method of claim 9, further comprising:
determining whether a goal for a user of the health tracking system has been met by comparing the calculated first metric to a threshold value therefor.

11. The method of claim 10 wherein said calculated first metric is displayed on the display screen in a first color indicative of said user not meeting said goal, and wherein said recalculated first metric is displayed on the display screen in a second color indicative of said user meeting said goal.

12. The method of claim 9, wherein:
the nutritional data comprises a calorie amount;
the first metric comprises a total amount of calories consumed by a user;
the act of calculating the first metric further comprises adding the caloric amount of each of the plurality of consumable item selections; and
the act of recalculating the first metric comprises purposeful omission of the caloric amount of the identified at least one of the plurality of consumable items.

13. The method of claim 9, wherein:
the nutritional data comprises a macronutrient amount;
the first metric comprises a total amount of the macronutrient consumed by a user;
the act of calculating the first metric further comprises adding the macronutrient amount of each of the plurality of consumable item selections; and
the act of recalculating the first metric comprises purposeful omission of the macronutrient amount of the identified at least one of the plurality of consumable items.

14. The method of claim 9, wherein the period of time comprises at least one of: a particular week, a particular day, and period associated to a particular meal on a particular day.

15. The method of claim 9, wherein the act of identifying further comprises:
receiving at the health tracking device, an input from a user selecting the at least one of the plurality of consumable item selections to be purposefully omitted; and
flagging the selected at least one of the plurality of consumable item selections based on the received input.

16. A method of operating a health tracking system, the method comprising:
receiving a plurality of consumable item selections associated with a period of time, each of the plurality of consumable item selections associated with a data record in a database, each data record in the database comprising nutritional data regarding a consumable item to which the data record corresponds, said nutritional data including a nutritional value;
calculating a first metric based on the nutritional data regarding the plurality of consumable item selections, the calculation of the first comprising an aggregate of the nutritional values associated with the plurality of consumable item selections;
determining that a user has not achieved a goal based on the calculated first metric exceeding a threshold value;
displaying the first metric on a display screen of the health tracking system along with the nutritional value of each of the plurality of consumable item selections and a first indicia that the threshold value has been exceeded;
after displaying the first metric on the display screen, receiving an input from a user selecting at least one of the plurality of consumable item selections to be purposefully omitted;

flagging the selected at least one of the plurality of consumable item selections to be purposefully omitted based on the received input;

recalculating the first metric based on the nutritional data regarding the plurality of consumable item selections, the recalculation of the first metric comprising purposeful omission of the nutritional data of the flagged at least one of the plurality of consumable items;

determining that a user goal has achieved a goal based on the recalculated first metric not exceeding the threshold value;

after recalculating the first metric, displaying the recalculated first metric on the display screen along with a second indicia that the threshold not been exceeded, and displaying the flagged at least one of the plurality of consumable items on the display screen but omitting to display the nutritional value of the flagged at least one of the plurality of consumable items such that the nutritional value of said flagged at least one consumable item is hidden; and generating a recommended alternative for said flagged at least one of the plurality consumable item selections, wherein said recommended alternative is at least one data record in the database, and wherein the recommended alternative is determined to be associated with healthier nutritional data than said flagged at least one of the plurality of consumable item selections.

17. The method of claim 16 wherein the nutritional value for said recommended alternative is less than the nutritional value for said flagged at least one of the plurality of consumable item selections.

18. The method of claim 16 further comprising receiving a long press of said flagged at least one consumable item on the display screen, and in response to receipt of said long press, temporarily revealing the hidden nutritional value of said flagged at least one consumable item on the display screen.

19. The method of claim 16 further comprising displaying said recommended alternative on the display screen of the health tracking device.

* * * * *